(12) United States Patent
Li et al.

(10) Patent No.: US 8,278,627 B2
(45) Date of Patent: Oct. 2, 2012

(54) SAMPLE FEEDING DEVICE FOR TRACE DETECTOR AND TRACE DETECTOR WITH SAMPLE FEEDING DEVICE

(75) Inventors: Yuanjing Li, Beijing (CN); Zhiqiang Chen, Beijing (CN); Qingjun Zhang, Beijing (CN); Shaoji Mao, Beijing (CN); Ziran Zhao, Beijing (CN); Yinong Liu, Beijing (CN); Shiping Cao, Beijing (CN); Yan Zheng, Beijing (CN); Jianping Chang, Beijing (CN); Xiang Zou, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 0 days.

(21) Appl. No.: 13/142,523

(22) PCT Filed: May 16, 2011

(86) PCT No.: PCT/CN2011/074079
§ 371 (c)(1),
(2), (4) Date: Jun. 28, 2011

(65) Prior Publication Data
US 2012/0168620 A1  Jul. 5, 2012

(30) Foreign Application Priority Data

May 16, 2011 (CN) .......................... 2010 1 0619932

(51) Int. Cl.
*H01J 49/04* (2006.01)
*B01D 59/44* (2006.01)
*G01N 1/10* (2006.01)

(52) U.S. Cl. ........ 250/428; 250/435; 250/288; 250/281; 356/246

(58) Field of Classification Search .................. 250/428, 250/435, 288, 281, 282
See application file for complete search history.

(56) References Cited

U.S. PATENT DOCUMENTS

| | | | |
|---|---|---|---|
| 5,496,733 A * | 3/1996 | Spandau et al. | 436/52 |
| 5,764,356 A * | 6/1998 | Iwase et al. | 356/246 |
| 6,710,871 B1 * | 3/2004 | Goix | 356/318 |
| 2011/0139975 A1 * | 6/2011 | Peng et al. | 250/282 |

(Continued)

FOREIGN PATENT DOCUMENTS

CN  101113969 A  1/2008

(Continued)

OTHER PUBLICATIONS

Search Report from PCT Application No. PCT/CN2011/074079, dated Oct. 13, 2011, 5 pgs.

(Continued)

*Primary Examiner* — Nikita Wells
(74) *Attorney, Agent, or Firm* — Westman, Champlin & Kelly, P.A.

(57) ABSTRACT

A sample feeding device for a trace detector is disclosed. The sample feeding device comprises: a sample feeding chamber disposed in the sample feeding device to desorb a sample from a sample feeding member; and a valve assembly configured to fluidly communicate the sample feeding chamber with a drift tube of the trace detector during feeding sample. With the above configuration of the present invention, for example, the sensitivity of the detector can be increased by improving the permeation ratio of the sample. In addition, interior environment of the drift tube is isolated from exterior environment to avoid a drift region of the drift tube from being polluted. The important parameters, such as sensitivity, a position of a peak of a substance, a resolution, of the detector can be kept constant. As a result, operation reliability and consistency of the detector can be achieved.

10 Claims, 6 Drawing Sheets

FOREIGN PATENT DOCUMENTS

| | | |
|---|---|---|
| CN | 101471222 A | 7/2009 |
| DE | 42 25 495 A1 | 1/1994 |
| JP | 59000845 A | 1/1984 |

OTHER PUBLICATIONS

Written Opinion from PCT Application No. PCT/CN2011/074079, dated Oct. 13, 2011, 5 pgs.

\* cited by examiner

SAMPLE FEEDING DEVICE FOR TRACE DETECTOR AND TRACE DETECTOR WITH SAMPLE FEEDING DEVICE

CROSS-REFERENCE TO RELATED APPLICATION

This Application is a Section 371 National Stage Application of International Application No. PCT/CN2011/074079, filed 16 May 2011, not yet published, which claims the benefit of Chinese Patent Application No. 201010619932.6 filed on Dec. 31, 2010 in the State Intellectual Property Office of China, the contents/disclosure of which are incorporated herein by reference.

BACKGROUND OF THE INVENTION

1. Field of the Invention

The present invention relates to a sample feeding device for a trace detector and a trace detector with the sample feeding device.

2. Description of the Related Art

Currently commercially available detectors for safety inspection mainly detect harmful substances such as explosives and narcotics by ion mobility spectrometry. Such detectors comprise a sample feeding device. The sample feeding device can gasify and desorb solid particles or gas entering into the device. The gasified sample molecules are then introduced into an ionization region by air flow. After that, the ionized sample molecules enter into a drift region. The molecules are identified based on their drift time in the drift region. Most of commercially available detectors employ a semi-permeable membrane. The semi-permeable membrane can isolate an interior of a drift tube from the outside environment to prevent dust and foreign substance molecules from entering into the drift tube so as to ensure the cleanness of the interior of the drift. Only molecules (generally large molecules) having certain property can permeate the semi-permeable membrane to enter into the drift tube. The semi-permeable membrane exhibits a certain permeation ratio. A general permeation ratio is only around 10%. Therefore, most of the sample molecules are lost outside the semi-permeable membrane and few sample molecules enter into the drift tube, which results in considerable reduction in sensitivity of the detectors. In addition, the semi-permeable membrane generally operates at a high temperature, which requires a system to provide the semi-permeable membrane with an additional operation environment and heat. As a result, the operation power of the system is increased. If the detector is portable, power sustaining time of a battery will reduce. A detector without a semi-permeable membrane will produce a complex background peak since the drift region is in direct communication with the atmosphere environment and thus the interior environment in the detector tends to be polluted. In addition, a peak of a substance greatly varies and a position of the peak is unstable with the change of the exterior environment so that stability of detection operation is seriously degraded.

SUMMARY OF THE INVENTION

It is therefore an object of the present invention to provide a sample feeding device for a trace detector, such as an ion mobility spectrometer (IMS), and a trace detector, such as an ion mobility spectrometer (IMS), having the sample feeding device, which can increase sensitivity of the trace detector, such as an ion mobility spectrometer (IMS).

According to an aspect of the present invention, there is provided a sample feeding device for a trace detector. The sample feeding device comprises a sample feeding chamber disposed in the sample feeding device to desorb a sample from a sample feeding member; and a valve assembly configured to fluidly communicate the sample feeding chamber with a drift tube of the trace detector during feeding sample.

According to another aspect of the present invention, the valve assembly comprises a sealing member; and a flange disposed on an inner wall of the sample feeding chamber, wherein the sample feeding chamber fluidly communicates with the drift tube of the trace detector by separating the sealing member from the flange and the sample feeding chamber is isolated from the drift tube of the trace detector by bringing the sealing member into contact with the flange.

According to a further aspect of the present invention, the flange divides the sample feeding chamber into a first sample feeding chamber and a second sample feeding chamber. The first sample feeding chamber is configured to be in fluid communication with the trace detector and the second sample feeding chamber is configured to desorb the sample from the sample feeding member, the first sample feeding chamber fluidly communicates with the second sample feeding chamber by separating the sealing member from the flange and the first sample feeding chamber is isolated from the second sample feeding chamber by bringing the sealing member into contact with the flange.

According to a further aspect of the present invention, the sample feeding device further comprises a sample feeding port in communication with the second sample feeding chamber.

According to a still further aspect of the present invention, the second sample feeding chamber is isolated from the sample feeding port while the first sample feeding chamber fluidly communicates with the second sample feeding chamber by separating the sealing member from the flange, and thereby the first sample feeding chamber and the second sample feeding chamber are isolated from an outside of the sample feeding device.

According to a further aspect of the present invention, the sealing member comprises a cylindrical part; a head connected with the cylindrical part, the head having an annular groove; and a seal ring disposed in the annular groove which is configured to contact with the flange to isolate the first sample feeding chamber from the second sample feeding chamber.

According to a further aspect of the present invention, the sample feeding device further comprises an actuating member configured to move the sealing member to fluidly communicate the first sample feeding chamber with the second sample feeding chamber or to isolate the first sample feeding chamber from the second sample feeding chamber.

According to a further aspect of the present invention, the actuating member comprises a carriage having opposite outer walls substantially parallel to each other; and slide rods disposed on the outer walls, the carriage being connected with the cylindrical part of the sealing member; and an actuating frame having grooves in which the slide rods are slideably disposed, and thereby when the actuating frame moves, the carriage is actuated to move by cooperation of the slide rods and the grooves so as to move the sealing member.

According to another aspect of the present invention, there is provided a trace detector. The trace detector comprises the sample feeding device; a drift tube for ionizing and charging the sample from the sample feeding device and drifting the ionized sample; and a Faraday plate configured to collect the ionized sample.

With the above configuration of the present invention, the sensitivity of the detector can be increased by improving a permeation ratio of the sample. In addition, interior environment of the drift tube is isolated from exterior environment to avoid a drift region of the drift tube from being polluted. The important parameters, such as sensitivity, a position of a peak of a substance, a resolution, of the detector can be kept constant. As a result, stableness and consistency of the detector can be achieved.

According to another aspect of the present invention, a sample feeding device comprises a linkage, a single sample feeding chamber (airtight chamber), a is sample molecule desorption device and a sample feeding port. The airtight sample feeding chamber is in directly communication with a gas path located within a drift tube. The device can control the sample feeding chamber to communicate with an outside atmosphere or not to communicate with the outside atmosphere. When the detector does not operate, that is, no sample is fed, the linkage enables the airtight sample feeding chamber to be isolated from the outside atmosphere so that the gas path within the drift tube is in a sealed state and is isolated from the outside environment. The linkage is activated by an outside signal, that is, by a triggering signal in response to feeding sample. After the linkage is activated, the airtight sample feeding chamber communicates with the outside atmosphere so that the sample molecules can be directly entrained into the drift tube from outside of the drift tube. After the sample molecules enter into the drift tube, they are firstly ionized. The charged sample molecules pass through a drift region and then are collected by a Faraday plate. The sample is identified based on drift time.

Since the sample feeding device does not comprise a semipermeable membrane or a device having a particular permeation ratio, desorbed or gaseous sample molecules can freely enter into the drift tube. The sample feeding efficiency is greatly improved so that sensitivity is radically increased. In addition, the airtight sample feeding chamber enables an interior of the drift tube to be in a sealed state, that is, in a non-sample feeding state for a long time. Foreign substance is prevented from entering into the drift tube and thus the drift tube can be kept in a clean state to ensure substance differentiating ability of the drift tube and to still keep the substance differentiating ability uniform in different environments.

DETAILED DESCRIPTION OF THE EMBODIMENTS

The embodiments are described below in order to further explain the present invention by referring to the figures.

Referring to FIGS. 1-11, a trace detector such as an ion mobility spectrometer, according to the present invention comprises a sample feeding device 100; a drift tube for ionizing and charging a sample from the sample feeding device 100 and drifting the ionized and charged sample; and a Faraday plate configured to collect the ionized and charged sample.

Figure 1:
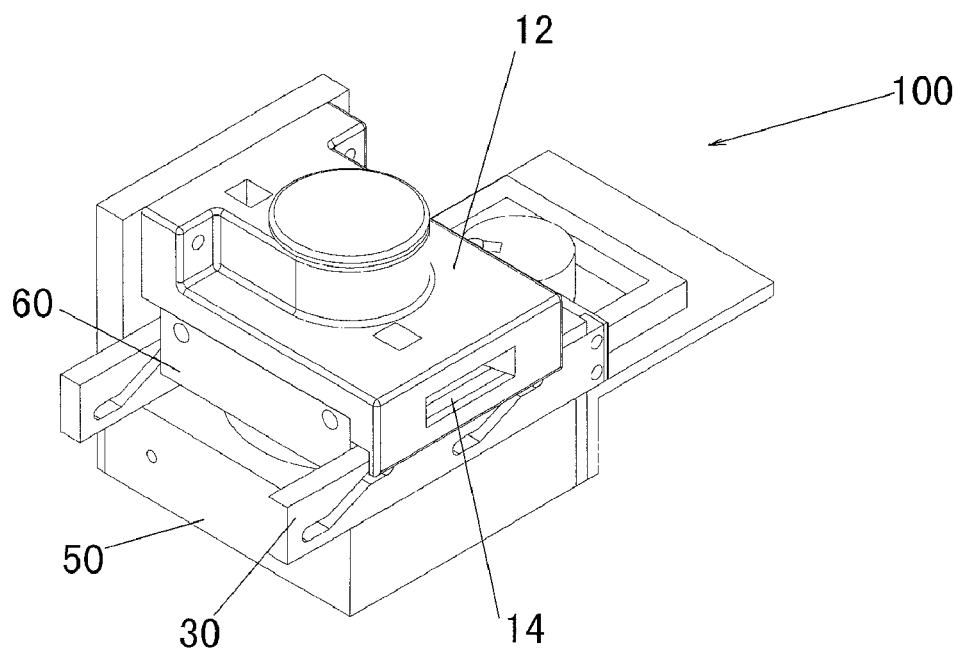
FIG. 1 is a schematic perspective view of a sample feeding device according to an embodiment of the present invention.
Figure 2:
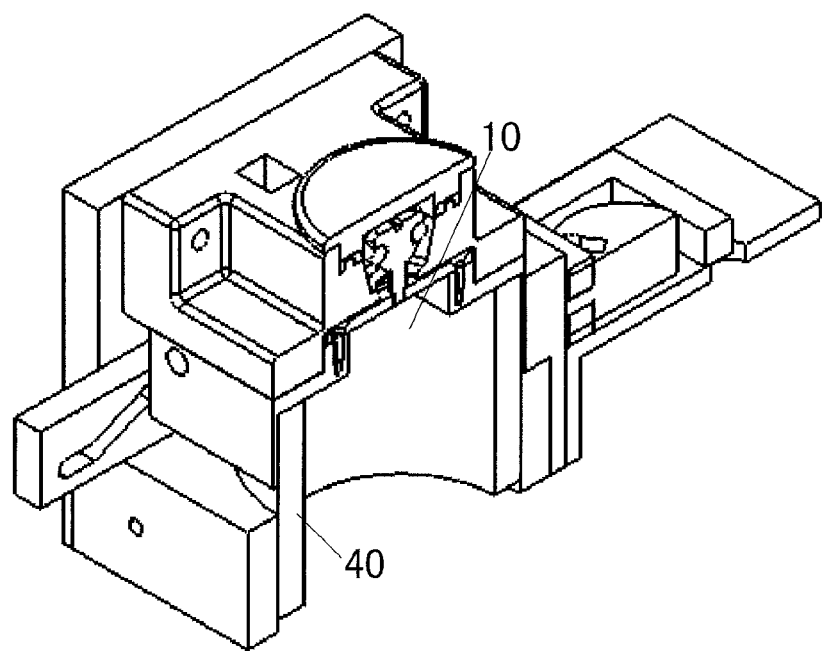
FIG. 2 is a schematic perspective cut-away view of the sample feeding device of FIG. 1.
Figure 3:
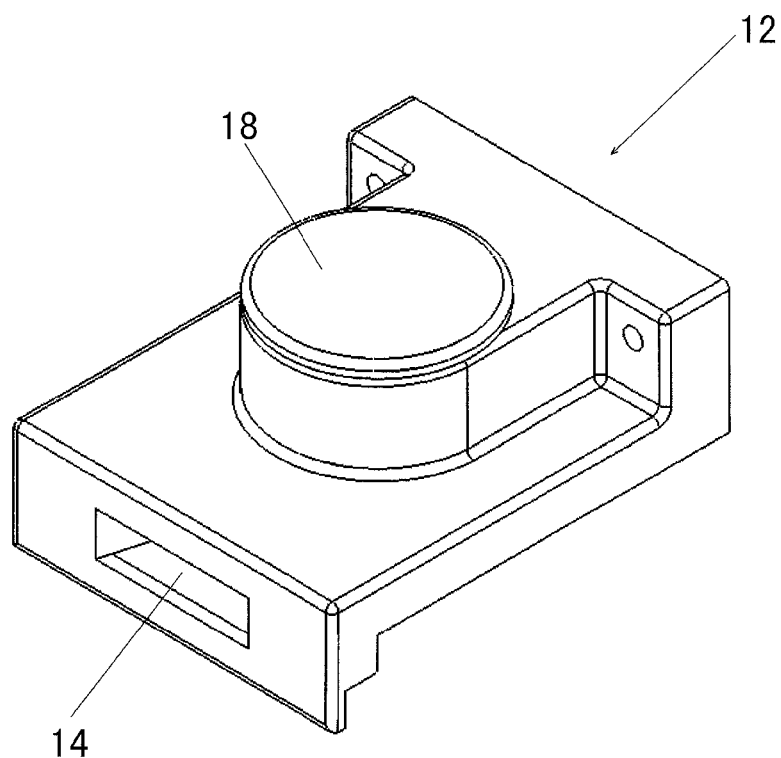
FIG. 3 is a schematic perspective view of an airtight sample feeding chamber assembly of the sample feeding device of FIG. 1.
Figure 4:
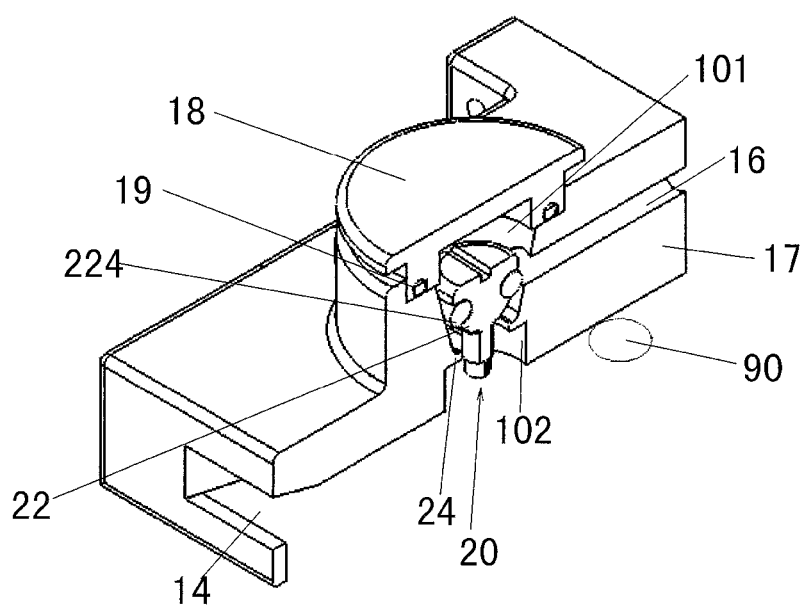
FIG. 4 is a schematic perspective cut-away view of the airtight sample feeding chamber assembly of FIG. 3.

As illustrated in FIGS. 1-11, the sample feeding device 100 comprises a sample feeding chamber 10 disposed in the sample feeding device 100 to desorb a sample from a sample feeding member; and a valve assembly 20 configured to fluidly communicate the sample feeding chamber 10 with the drift tube of the trace detector during feeding sample. As illustrated in FIGS. 3-4, the sample feeding chamber 10 is formed by a sample feeding chamber assembly 12 and a sample feeding port 14 is formed in the sample feeding chamber assembly 12. In addition, a gas path 16 is formed in the sample feeding chamber assembly 12 to communicate with the drift tube and the sample feeding chamber 10.

As illustrated in FIGS. 1-11, the sample feeding device 100 further comprises an actuating frame 30, a heating assembly 40, and a base 50. As illustrated in FIGS. 1-2, a gas path located within the drift tube communicates with the sample feeding port through the airtight sample feeding chamber 10.

The valve assembly 20 comprises a sealing member 22; and a flange 24 disposed on an inner wall of the sample feeding chamber 10. The sample feeding chamber 10 fluidly communicates with the drift tube of the trace detector by separating the sealing member 22 from the flange 24 and the sample feeding chamber 10 is isolated from the drift tube of the trace detector by bringing the sealing member 22 into contact with the flange 24. The flange 24 divides the sample feeding chamber 10 into a first sample feeding chamber 101 and a second sample feeding chamber 102. The first sample feeding chamber 101 is configured to be in fluid communication with the trace detector, that is, to be in fluid communication with the gas path 16. The second sample feeding chamber 102 is configured to desorb the sample from the sample feeding member. The first sample feeding chamber 101 fluidly communicates with the second sample feeding chamber 102 by separating the sealing member 22 from the flange 24 and the first sample feeding chamber 101 is isolated from the second sample feeding chamber 102 by bringing the sealing member 22 into contact with the flange 24. The sample feeding port 14 is in communication with the second sample feeding chamber 102.

Figure 6:
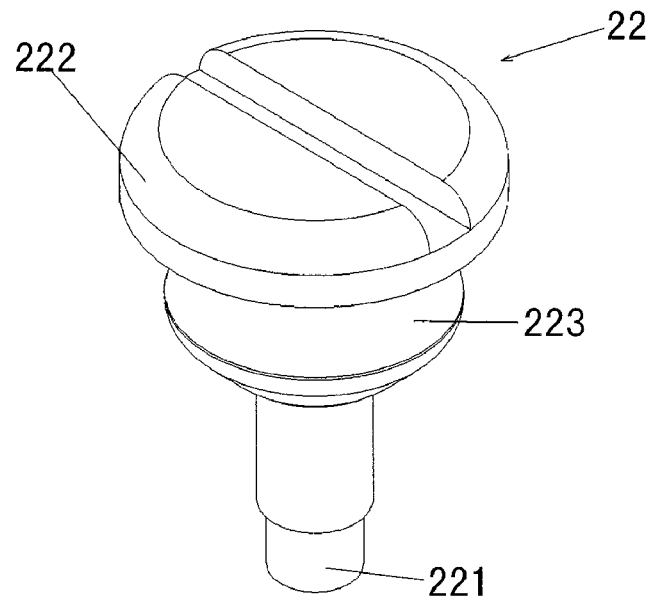
FIG. 6 is a schematic perspective view of a sealing member of the sample feeding device of FIG. 1.

As illustrated in FIG. 6, the sealing member 22 comprises a cylindrical part 221; a head 222 connected with the cylindrical part, the head having an annular groove 223; and a seal ring 224 (referring to FIG. 4) disposed in the annular groove 223. The seal ring 224 is configured to contact with the flange 24 to isolate the first sample feeding chamber 101 from the second sample feeding chamber 102.

The sample feeding chamber assembly 12 comprises a housing 17 and a top cover 18. The first sample feeding chamber 101 is formed by a seal ring 19, the sealing member 22, the flange 24, the top cover 18 and the housing 17. The seal ring is a circular ring formed of rubber such as medical silicone rubber and fluororubber, or polytetrafluoroethylene. The sealing member 22 is illustrated in FIG. 6. The head 222 has a shape of a pot. A groove 223 is formed at an intermediate portion of the head having the shape of a pot. The seal ring 224 is placed in the groove 223. The top cover 18 is a disk-shaped element. A groove is formed on a bottom of the disk-shaped element, and the seal ring 19 is placed in the groove. The top cover 18 is sealed against the housing 17 through the rubber seal ring 19 to enclose a space of the first sample feeding chamber 101.

Figure 5:
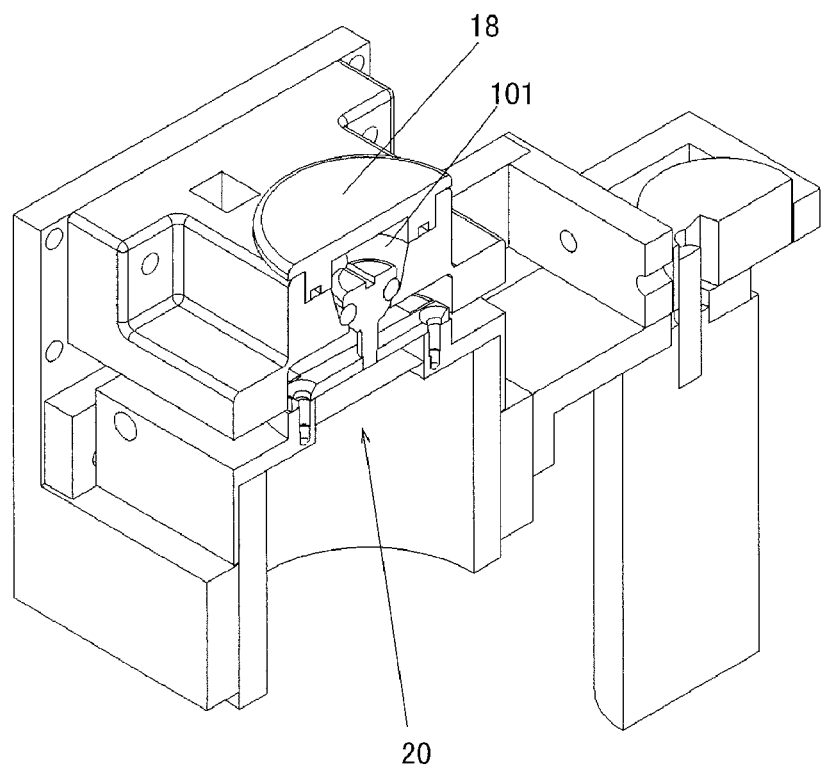
FIG. 5 is a schematic perspective cut-away view of the sample feeding device of FIG. 1 in a non-sample feeding state.

The housing 17 is hollow and has multiple functions. The housing 17 acts as a support for the entire sample feeding device, and comprises the sample feeding port 14, and the sample feeding chamber 10 formed by a hollow portion of the housing. A protrusion or the flange 24 is disposed at an intermediate portion of the sample feeding chamber. As illustrated in FIG. 4, the portion of the sample feeding chamber above the protrusion 24 is referred to as the first sample feeding chamber 101, and the portion of the sample feeding chamber below the protrusion 24 is referred to as the second sample feeding chamber 102. The first sample feeding chamber 101 is in communication with the interior of the drift tube through a hole. The second sample feeding chamber 102 is directly connected with the sample feeding port 14. The sample feeding port 14 is composed of a cuboid space of which an upper portion is in direct communication with the second sample feeding chamber 102. When the sample feeding device does not operate, a downward force, i.e. gravity, is applied to the sealing member 22 so that the seal ring 224 is pressed against the projection 24 within the housing. The first sample feeding chamber 101 and the second sample feeding chamber 102 are then isolated from each other and no gas flows between the first sample feeding chamber 101 and the second sample feeding chamber 102. In this case, the state of the sample feeding device is in a sate as illustrated in FIG. 5.

Figure 7:
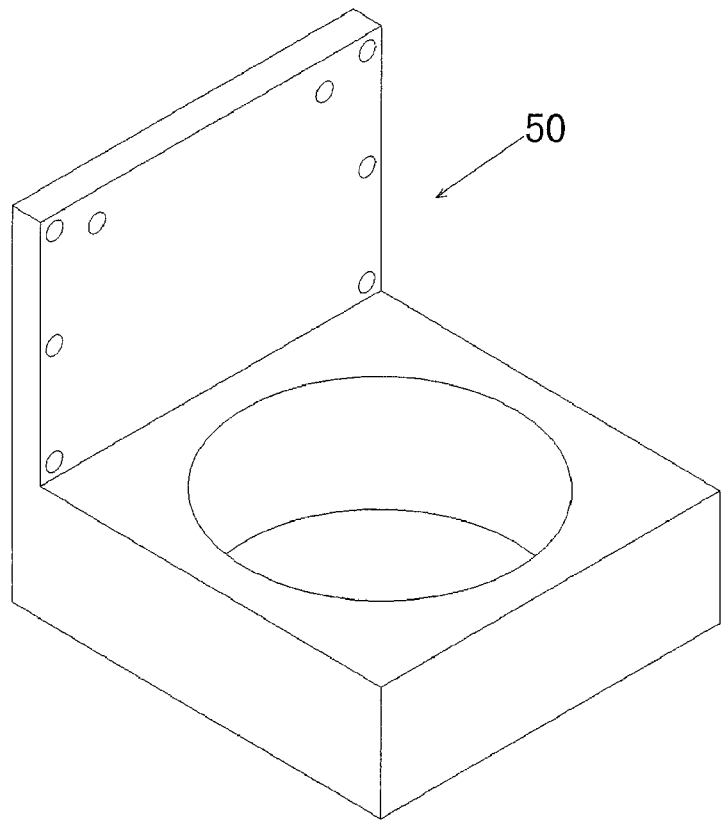
FIG. 7 is a schematic perspective view of a base of the sample feeding device of FIG. 1.
Figure 8:
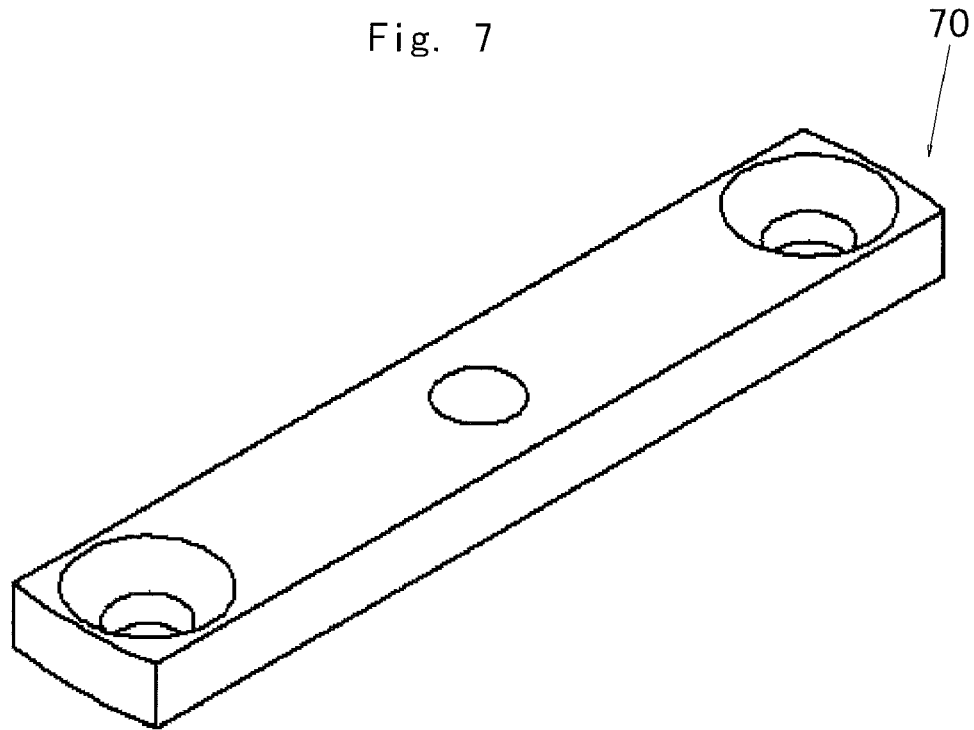
FIG. 8 is a schematic perspective view of a sealing member support of the sample feeding device of FIG. 1.
Figure 9:
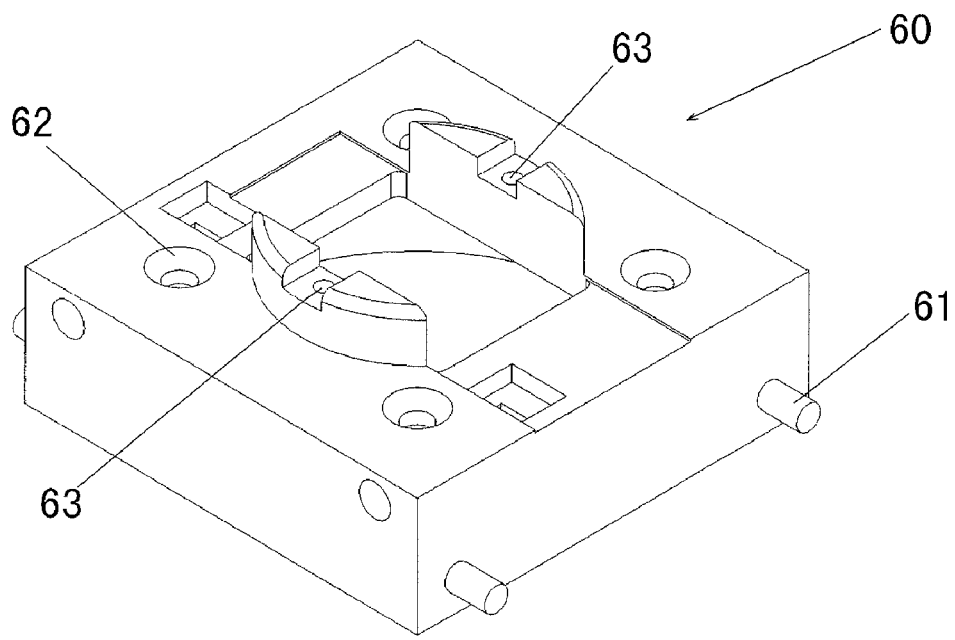
FIG. 9 is a schematic perspective view of a carriage of the sample feeding device of FIG. 1.
Figure 10:
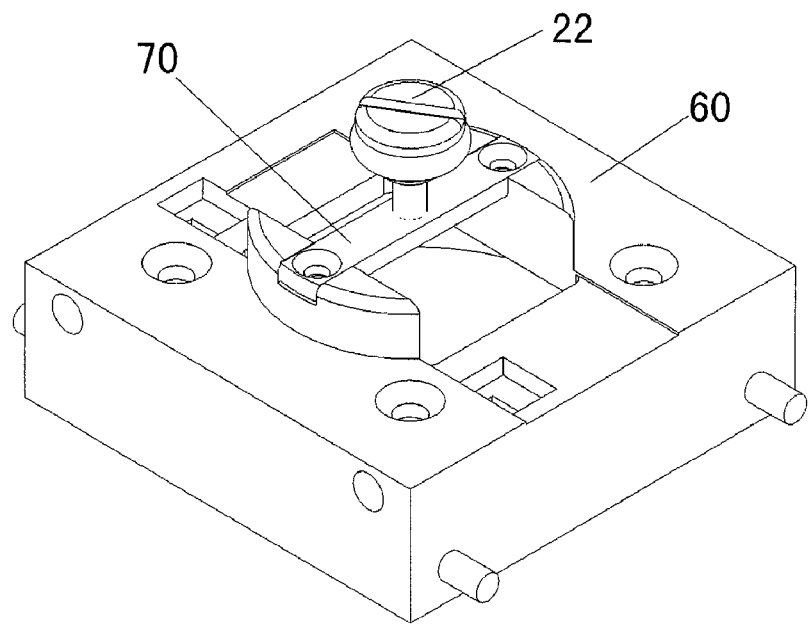
FIG. 10 is a schematic perspective view of the sealing member, the sealing member support, and the carriage in an assembled state.
Figure 11:
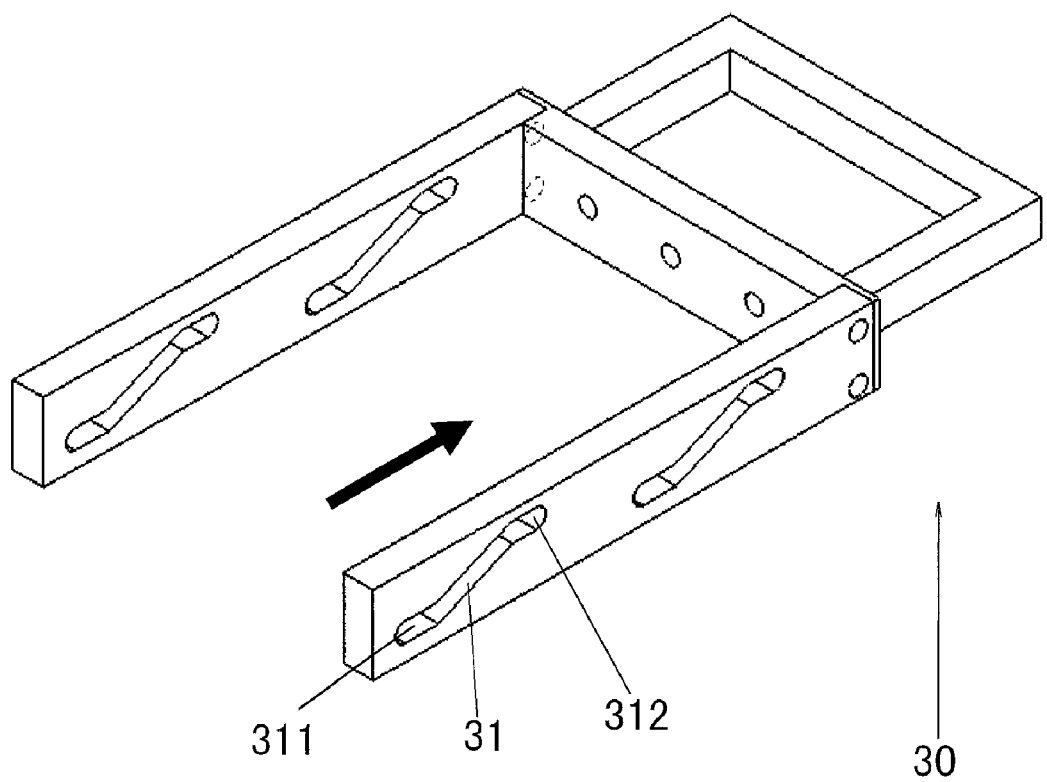
FIG. 11 is a schematic perspective view of an actuating frame of the sample feeding device of FIG. 1.

As illustrated in FIG. 7, the housing 17 is secured to a side of the base 50 by means of screws located on a side of the housing to constitute an integral housing. The cylindrical part 221 of the sealing member 22 is fastened to a sealing member support 20 (by means of screws). As illustrated in FIG. 9, the sealing member support 70 (referring to FIG. 8) is mounted to the carriage 60 (referring to FIG. 9) through two screw holes 63 located at a center of the carriage 60. The carriage 60 is fastened to the heating assembly 40 through four screw holes 62 located at four corners of the carriage 60. The heating assembly 40 is provided with a case and a heating element disposed in the case. The case may be polytetrafluoroethylene heater sheath.

With the above configuration, the sealing member 22, the sealing member support 70, the carriage 60, and the heating assembly 40 are integrated, and move upwards or downwards integrally. Four slide rods 61 are disposed on sides of the carriage 60 and placed in grooves 31 of the actuating frame 30 (referring to FIG. 11). When the actuating frame 30 slides in a same horizontal plane, the carriage 60 moves upwards or downwards with the slide of the actuating frame to move the sealing member 22 upwards or downwards. The actuating frame 30 is exteriorly connected with a power source such as a motor. The actuating frame 30 moves horizontally under the action of an external force.

The heater may be located within the heater sheath. The heater may be heating means such as an electric heater or laser. When no sample is fed, the heater is at a normal atmospheric temperature, or in a semi-heating state, that is, at a temperature lower than a thermal desorption temperature and greater than an ambient temperature. When a sample is fed, the sample feeding device begins to operate. The sample feeding device heats the fed sample test paper to a high temperature quickly to thermally desorb the sample from the test paper into gas rapidly.

When the sample feeding device does not operates, that is, no sample is fed, the first sample feeding chamber 101 is isolated from the exterior environment and the system is in a state as shown in FIG. 5. In this case, the interior of the drift tube is isolated from the outside, in a clean and high-temperature environment, and is not affected by gases from the exterior environment. When the sample feeding device operates, a sample feeding test paper with sample is inserted into the sample feeding device from the sample feeding port 14, and placed onto a top surface of the carriage 60. A sensor located under a lower end of the carriage 60 at a position 90 outputs a triggering signal to the system. The system sends the signal to the power source such as a motor. The power source such as a motor translates the actuating frame 30 so that the carriage 60 carrying the sample test paper lifts by a height measured upwards from a low groove part 311 of the actuating frame 30 to a high groove part 312 of the actuating frame 30. In this case, the sealing member 22 ascends from a bottom end to a top end within the airtight sample feeding chamber 10. As a result, the first sample feeding chamber 101 is in communication with the outside of the first sample feeding chamber so that the drift tube is in communication with the outside of the drift tube, and the top surface of the carriage 60 is brought into contact with a bottom surface of the housing 17 so that the second sample feeding chamber 102 is isolated from the sample feeding port 14, that is, the sample feeding chamber 10 is isolated from the outside of the sample feeding chamber. While receiving the triggering signal or after a delay from receiving the triggering signal, the heating assembly located at the bottom of the sample feeding device begins to operate in a manner such as thermal radiation or convection to gasify and desorb the sample from the sample feeding test paper quickly. Under the action of gas flow, gas entraining the sample enters into the first sample feeding chamber 101 across both sides of the sealing member support 70, and then flows into the ionization region within the drift tube through the hole for gas. The sample molecules are ionized in the ionization region, and then the charged sample particles enter into the drift region under the effect of an electric field. Different molecules are identified based on their different drift times.

According to the above embodiment, the second sample feeding chamber is isolated from the sample feeding port while the first sample feeding chamber fluidly communicates with the second sample feeding chamber by separating the sealing member from the flange, and thereby the first sample feeding chamber and the second sample feeding chamber are isolated from the outside of the sample feeding device. Apparently, the solution can be achieved in other manners. For example, a second valve assembly may be provided to fluidly communicate the second sample feeding chamber with the sample feeding port or to isolate the second sample feeding chamber from the sample feeding port. By operating the second valve assembly in cooperation with the valve assembly 20 simultaneously, the second sample feeding chamber is isolated from the sample feeding port while the first sample feeding chamber and the second sample feeding chamber communicates with each other. Therefore, the present invention is not limited to the above embodiment.

In addition, the carriage 60 and the like move upwards or downwards as illustrated in the figures. However, this is only for the purpose of convenience in description. The carriage 60 and the like may move in any direction.

Furthermore, the sample feeding test paper may not be placed on the top surface of the carriage 60, but may be placed in a sample feeding test paper fixing part disposed on the carriage 60. Therefore, although the carriage 60 moves for example in a right-left direction rather than upwards or downwards, the sample feeding test paper will not fall from the carriage 60.

In the above embodiment, the top surface of the carriage 60 is brought into contact with the bottom surface of the housing 17 so that the second sample feeding chamber 102 is isolated from the sample feeding port 14 (in this case, the carriage 60 has no center hole. However, the carriage 60 may have the center hole as shown in the figures. After the test paper is inserted into the sample feeding port, the first sample feeding chamber 101 is in communication with the second sample feeding chamber 102, the first sample feeding chamber 101 and the second sample feeding chamber 102 is separated from the exterior environment through the test paper, and gas exchanges between the first and second sample feeding chambers 101 and 102 and the exterior environment.

What is claimed is:

1. A sample feeding device for a trace detector, comprising:
   a sample feeding chamber disposed in the sample feeding device to desorb a sample from a sample feeding member; a flange disposed on an inner wall of the sample feeding chamber, wherein the flange divides the sample feeding chamber into a first sample feeding chamber and a second sample feeding chamber, wherein the first sample feeding chamber is configured to be in fluid communication with the trace detector and the second sample feeding chamber is configured to desorb the sample from the sample feeding member; and
   a valve assembly configured to fluidly communicate the sample feeding chamber with a drift tube during feeding sample.

2. The sample feeding device of claim 1, wherein the valve assembly comprises a sealing member; and a flange disposed on an inner wall of the sample feeding chamber, wherein the sample feeding chamber fluidly communicates with the drift tube of the trace detector by separating the sealing member from the flange and the sample feeding chamber is isolated from the drift tube of the trace detector by bringing the sealing member into contact with the flange.

3. The sample feeding device of claim 2, wherein the flange divides the sample feeding chamber into a first sample feeding chamber and a second sample feeding chamber, wherein the first sample feeding chamber is configured to be in fluid communication with the trace detector and the second sample feeding chamber is configured to desorb the sample from the sample feeding member, and wherein the first sample feeding chamber fluidly communicates with the second sample feeding chamber by separating the sealing member from the flange and the first sample feeding chamber is isolated from the second sample feeding chamber by bringing the sealing member into contact with the flange.

4. The sample feeding device of claim 3, further comprising a sample feeding port in communication with the second sample feeding chamber.

5. The sample feeding device of claim 4, wherein the second sample feeding chamber is isolated from the sample feeding port while the first sample feeding chamber fluidly communicates with the second sample feeding chamber by separating the sealing member from the flange, and thereby the first sample feeding chamber and the second sample feeding chamber are isolated from an outside of the sample feeding device.

6. The sample feeding device of claim 3, wherein the sealing member comprises a cylindrical part; a head connected with the cylindrical part, the head having an annular groove; and a seal ring disposed in the annular groove, and wherein the sealing ring is configured to contact with the flange to isolate the first sample feeding chamber from the second sample feeding chamber.

7. The sample feeding device of claim 6, further comprising:
   an actuating member configured to move the sealing member to fluidly communicate the first sample feeding chamber with the second sample feeding chamber or to isolate the first sample feeding chamber from the second sample feeding chamber.

8. The sample feeding device of claim 7, wherein the actuating member comprises:
   a carriage having opposite outer walls substantially parallel to each other; and
   slide rods disposed on the outer walls, the carriage being connected with the cylindrical part of the sealing member; and
   an actuating frame having grooves in which the slide rods are slideably disposed, and thereby when the actuating frame moves, the carriage is actuated to move by cooperation of the slide rods and the grooves so as to move the sealing member.

9. A trace detector, comprising:
   the sample feeding device of claim 1;
   a drift tube for ionizing the sample from the sample feeding device and drifting the ionized sample particles; and
   a Faraday plate configured to collect the ionized sample particles.

10. The trace detector of claim 9, wherein the trace detector is an ion mobility spectrometer.

* * * * *